(12) United States Patent
Lesh

(10) Patent No.: US 7,794,444 B2
(45) Date of Patent: Sep. 14, 2010

(54) CATHETER SYSTEM AND METHODS FOR DELIVERY OF THERAPEUTIC CELLS TO CARDIAC TISSUE

(75) Inventor: Michael D. Lesh, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 89 days.

(21) Appl. No.: 10/639,896

(22) Filed: Aug. 12, 2003

(65) Prior Publication Data

US 2004/0054335 A1 Mar. 18, 2004

Related U.S. Application Data

(63) Continuation of application No. 09/797,483, filed on Feb. 28, 2001, now Pat. No. 6,716,196, which is a continuation of application No. 08/403,553, filed on Mar. 14, 1995, now abandoned, which is a continuation of application No. 08/100,086, filed on Jul. 30, 1993, now abandoned.

(51) Int. Cl.
*A61M 31/00* (2006.01)
*A61M 5/178* (2006.01)
*A61M 5/32* (2006.01)
*A61M 25/00* (2006.01)

(52) U.S. Cl. .................. 604/506; 604/164.01; 604/174; 604/264; 604/523

(58) Field of Classification Search ......... 607/126–128, 607/119–122; 604/272, 264, 274, 523, 104, 604/158, 164.01, 175, 174, 131, 500, 506, 604/95.04, 522, 164.04; 128/DIG. 6; 600/435, 600/3, 12

See application file for complete search history.

(56) References Cited

U.S. PATENT DOCUMENTS

| 3,097,647 A | 7/1963 | Roehr |
| 3,508,545 A | 4/1970 | Prather et al. |
| 3,938,502 A | 2/1976 | Bom |
| 4,112,952 A | 9/1978 | Thomas et al. |

(Continued)

FOREIGN PATENT DOCUMENTS

WO WO 92/10142 6/1992

(Continued)

OTHER PUBLICATIONS

Avatal, B. et al. (1991). "A New Technique for AV Nodal Modification Using Perinodal Injection of a Sclerosing Agent," *JACC* 17(2):174A.

(Continued)

*Primary Examiner*—Nicholas D Lucchesi
*Assistant Examiner*—Nathan R Price
(74) *Attorney, Agent, or Firm*—Morrison & Foerster LLP

(57) ABSTRACT

This is a method and an apparatus for the introduction of therapeutic compounds into tissue, particularly cardiac tissue. The apparatus includes a catheter having an elongated flexible body and a tissue infusion apparatus including a hollow infusion needle configured to secure the needle into the tissue when the needle is at least partially inserted into the tissue to help prevent inadvertent removal of the needle from the tissue. This permits the selected therapeutic compound to be delivered to a specific site. The catheter may also include a visualization assembly including a transducer at the distal end of the body.

6 Claims, 6 Drawing Sheets

U.S. PATENT DOCUMENTS

| | | | |
|---|---|---|---|
| 4,280,512 A | 7/1981 | Karr et al. | |
| 4,559,039 A | 12/1985 | Ash et al. | |
| 4,576,177 A | 3/1986 | Webster, Jr. | |
| 4,578,061 A | 3/1986 | Lemelson | |
| 4,641,649 A | 2/1987 | Walinsky et al. | |
| H356 H | 11/1987 | Stokes et al. | |
| 4,747,405 A | 5/1988 | Leckrone | |
| 4,759,746 A | 7/1988 | Straus | |
| 4,760,845 A | 8/1988 | Kovalcheck | |
| 4,774,958 A | 10/1988 | Feinstein | |
| 4,790,311 A | 12/1988 | Ruiz | |
| 4,807,620 A | 2/1989 | Strul et al. | |
| 4,857,057 A | 8/1989 | Sanagi | |
| 4,898,577 A | 2/1990 | Badger et al. | |
| 4,900,303 A | 2/1990 | Lemelson | |
| 4,924,863 A | 5/1990 | Sterzer | |
| 4,940,064 A | 7/1990 | Desai | |
| 4,945,912 A | 8/1990 | Langberg | |
| 4,955,377 A | 9/1990 | Lennox et al. | |
| 4,960,134 A | 10/1990 | Webster, Jr. | |
| 4,998,933 A | 3/1991 | Eggers et al. | |
| 5,002,067 A | 3/1991 | Berthelsen et al. | |
| 5,030,204 A | 7/1991 | Badger | |
| 5,047,025 A | 9/1991 | Taylor et al. | |
| 5,057,105 A | 10/1991 | Malone et al. | |
| 5,057,494 A | 10/1991 | Sheffield | |
| 5,060,660 A | 10/1991 | Gambale et al. | |
| 5,084,026 A | 1/1992 | Shapiro | |
| 5,090,955 A | 2/1992 | Simon | |
| 5,104,393 A | 4/1992 | Isner et al. | |
| 5,119,832 A | 6/1992 | Xavier | |
| 5,130,141 A | 7/1992 | Law et al. | |
| 5,165,421 A | 11/1992 | Fleischhacker et al. | |
| 5,224,931 A | 7/1993 | Kumar | |
| 5,236,424 A | 8/1993 | Imran | |
| 5,246,437 A | 9/1993 | Abela | |
| 5,261,889 A | 11/1993 | Laine et al. | |
| 5,267,960 A | 12/1993 | Hayman et al. | |
| 5,281,218 A | 1/1994 | Imran | |
| 5,324,325 A | 6/1994 | Moaddeb | |
| 5,328,470 A * | 7/1994 | Nabel et al. | 604/101.03 |
| 5,336,252 A | 8/1994 | Cohen | |
| 5,346,991 A | 9/1994 | Roy et al. | |
| 5,353,800 A | 10/1994 | Pohndorf et al. | |
| 5,370,675 A | 12/1994 | Edwards et al. | |
| 5,399,346 A | 3/1995 | Anderson et al. | |
| 5,403,311 A | 4/1995 | Abele et al. | |
| 5,405,376 A | 4/1995 | Mulier et al. | |
| 5,409,688 A | 4/1995 | Quay | |
| 5,409,895 A | 4/1995 | Morishita et al. | |
| 5,431,649 A | 7/1995 | Mulier et al. | |
| 5,496,731 A | 3/1996 | Xu et al. | |
| 5,500,012 A | 3/1996 | Brucker et al. | |
| 5,531,676 A | 7/1996 | Edwards et al. | |
| 5,558,855 A | 9/1996 | Quay | |
| 5,580,575 A | 12/1996 | Unger et al. | |
| 5,588,432 A | 12/1996 | Crowley | |
| 5,612,057 A | 3/1997 | Lanza et al. | |
| 5,661,133 A | 8/1997 | Leiden et al. | |
| 5,693,622 A | 12/1997 | Wolff et al. | |
| 5,695,462 A | 12/1997 | Sutar et al. | |
| 5,698,531 A * | 12/1997 | Nabel et al. | 514/44 |
| 5,707,969 A * | 1/1998 | Nabel et al. | 514/44 |
| 5,756,476 A | 5/1998 | Epstein et al. | |
| 5,811,447 A * | 9/1998 | Kunz et al. | 514/411 |
| 5,827,703 A * | 10/1998 | Debs et al. | 514/44 |
| 5,830,209 A | 11/1998 | Savage et al. | |
| 5,840,031 A | 11/1998 | Crowley | |
| 5,980,516 A | 11/1999 | Mulier et al. | |
| 6,121,246 A | 9/2000 | Isner | |
| 6,283,951 B1 | 9/2001 | Flaherty et al. | |
| 6,297,220 B1 | 10/2001 | Leiden et al. | |
| 6,358,247 B1 | 3/2002 | Altman et al. | |
| 6,413,942 B1 | 7/2002 | Felgner et al. | |
| 6,716,196 B2 | 4/2004 | Lesh et al. | |

FOREIGN PATENT DOCUMENTS

| | | |
|---|---|---|
| WO | WO 93/04724 | 3/1993 |

OTHER PUBLICATIONS

Ayisi, K. et al. (1989). "Alcohol-Induced Coagulation Necrosis in Cardiac Tissue: A New Concept in the Surgical Management of Recurrent Ventricular Arrhythmias," *Thorac. Cardiovasc. Surgeon* 37:76-79.

DeMaio Jr., S.J. et al. (1990). "Treatment of Ventricular Tachycardia Induced Cardiogenic Shock by Percoronary Chemical Ablation," *Catheterization and Cardiovascular Diagnosis* 21:170-176.

Ellman, B.A. et al. (1984). "Renal Ablation with Absolute Ethanol," *Investigative Radiology* 19(5):416-423.

Friedman, D. et al. (1991). "Permanent Modification of A-V Function by Selective Intracoronary Ethanol Infusion in Patients with Refractory Supraventricular Tachycardia," *JACC* 17(2):174A.

Kay, G.N. et al. (1991). "A Prospective Evaluation of Intracoronary Ethanol Ablation of the Atrioventricular Conduction System," *JACC* 17(7):1634-1640.

Wetstein et, L. et al. (1985). "Propensity to Develop Ventricular Tachyarrhythmias: Differences in Homogeneous Versus Heterogeneous Myocardial Infarcts," *Puerto Rico Health Sciences J.* 4(2):79-89.

Borg, T.K. et al. (1981). "The Collagen Matrix of the Heart," *Federation Proc.* 40:2037-2041.

Buttrick, P.M. et al. (1992). "Behavior of Genes Directly Injected Into the Rat Heart In Vivo," *Circulation Research* 70:193-198.

Caulfield, J.B. (1979). "The Collagen Network of the Heart," *Laboratory Investigation* . 40(3):364-372.

Dolber, P.C. et al. (1987). "Thin Collagenous Septa in Cardiac Muscle," *Anatomical Record* 218:45-55.

Ellman, B.A. et al. (1980). "Renal Infarction with Absolute Ethanol," *Investigative Radiology* 15(4):318-322.

Ellman, B.A. et al. (1981). "Ablation of Renal Tumors with Absolute Ethanol: A New Techique," *Radiology* 141:619-626.

Factor, S.M. et al. (1988). "The Effects of Acutely Increased Ventricular Cavity Pressure on Intrinsic Myocardial Connective Tissue," *JACC* 12(6):1582-1589.

Guzman, R.J. et al. (1993). "Efficient Gene Transfer Into Myocardium by Direct Injection of Adenovirus Vectors," *Circ. Res.* 73:1202-1207.

Haines, D.E. et al. (1989). "Percoronary Ablation of Ventricular Myocardium: Pathologic Findings After Microfibrillar Collagen/Ethanol Embolization in Swine," *Circulation Supplement II* 80(4):II-324 (Abstract No. 1293).

Hanich, R.F. et al. (1988). "Inducible Sustained Ventricular Tachycardia 4 Years After Experimental Canine Myocardial Infarction: Electrophysiologic and Anatomic Comparisons with Early Healed Infarcts," *Circulation* 77(2):445-456.

Inoue, H. et al. (1987). "Intracoronary Ethyl Alcohol or Phenol Injection Ablates Aconitine-Induced Ventricular Tachycardia in Dogs," *JACC* 10(6):1342-1349.

Nellens, P. et al. (1992). "Transcoronary Chemical Ablation of Arrhythmias," *PACE* 15:1368-1373.

Robinson, R.F. et al. (1983). "Skeletal Framework of Mammalian Heart Muscle. Arrangement of Inter- and Pericellular Connective Tissue Structures," *Laboratory Investigation* 49(4):482-498.

Robinson, T.F. et al.(1988). "Coiled Perimysial Fibers of Papillary Muscle in Rat Heart: Morphology, Distribution, and Changes in Configuration," *Circ. Res.* 63:577-592.

Soonpa, M.H. et al. (1994). "Formation of Nascent Intercalated Disks Between Grafted Fetal Cardiomyocytes and Host Myocardium," *Science* 264:98-101.

von Harsdorf, R. et al. (1993). "Gene Injection Into Canine Myocardium as a Useful Model for Studying Gene Expression in the Heart of Large Mammals," *Circulation Research* 72:688-695.

Wang, P.J. et al. (1989). "A-V Nodal Ablation by Selective A-V Nodal Artery Infusion of Ethanol," *Circulation Supplement II* 80(4):II-324 (Abstract No. 1294).

Weismuller, P. et al. (1991). "Chemical Ablation by Subendocardial Injection of Ethanol Via Catherter-Preliminary Results in the Pig Heart," *European Heart J.* 12:1234-1239.

Losordo, D. et al. (1998). "Gene Therapy for Myocardial Angiogenesis: Initial Clinical Results with Direct Myocardial Injection of phVEGF$_{165}$ as Sole Therapy for Myocardial Ischemia," *Circulation* 98:2800-2804.

March, K. L. ed. (1997). "Delivery of Myoblasts to the Myocardium" *In Gene Transfer in the Cardiovascular System: Experimental Approaches and Therapeutic Implications.* Kluwer Academic Publishers: Norwell, Massachusetts, pp. 359-360.

Vale, P. R. et al. (1999). "Catheter-Based Myocardial Gene Transfer Utilizing Nonfluoroscopic Electromechanical Left Ventricular Mapping," *J Amer Coll Cardiology* 34(1):246-254.

\* cited by examiner

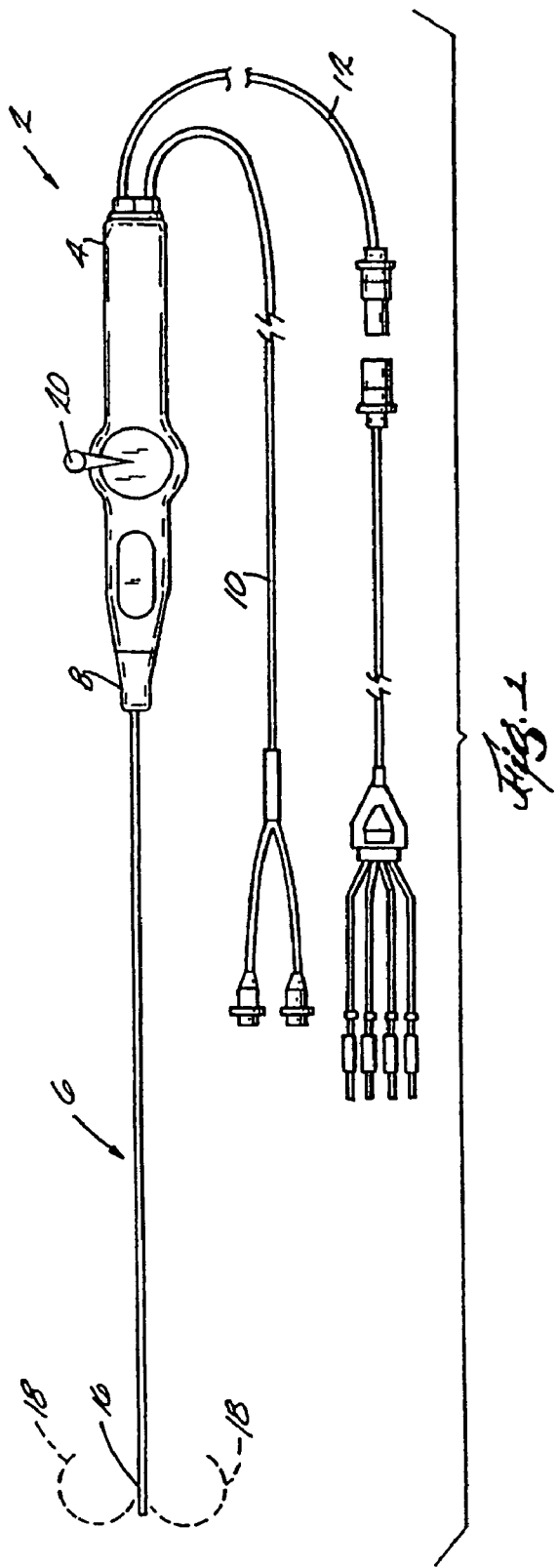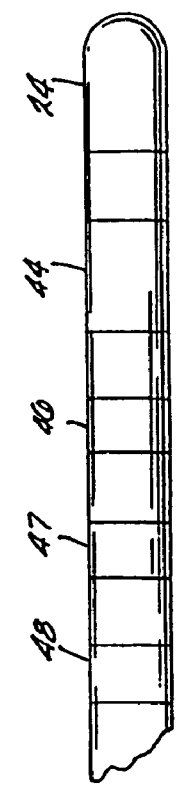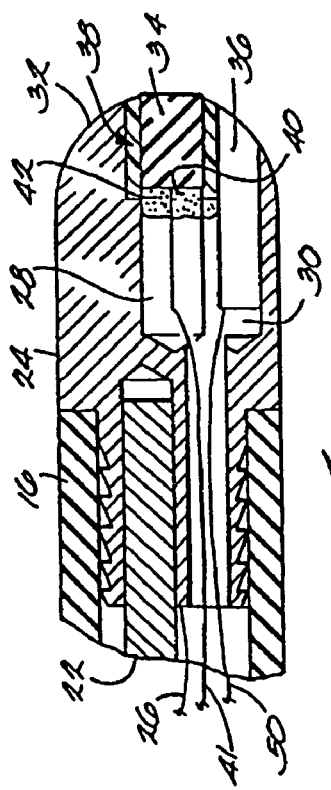

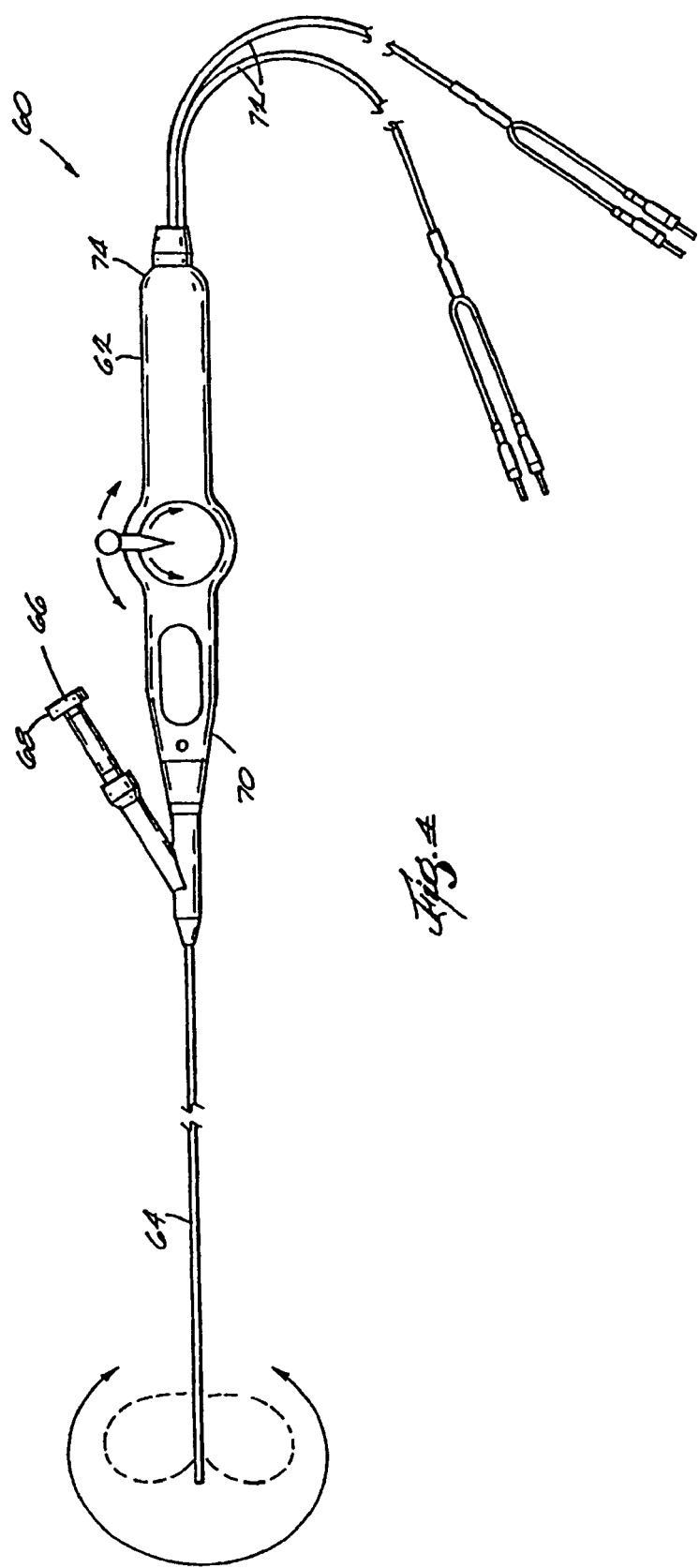

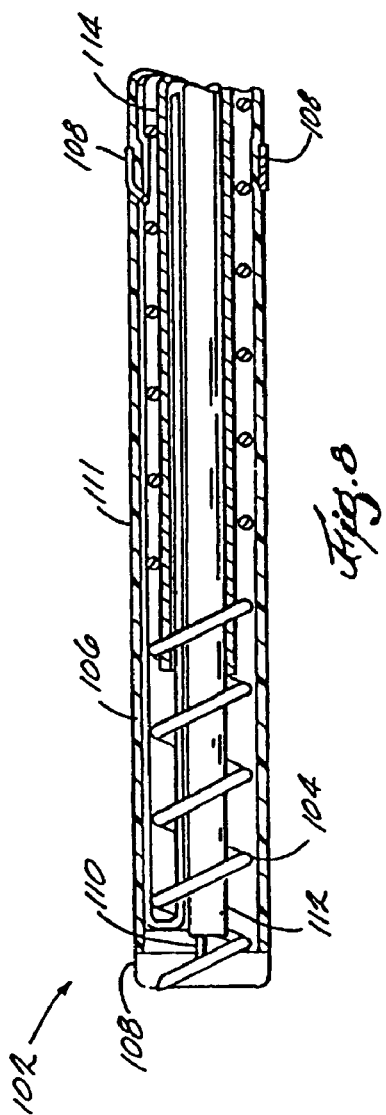
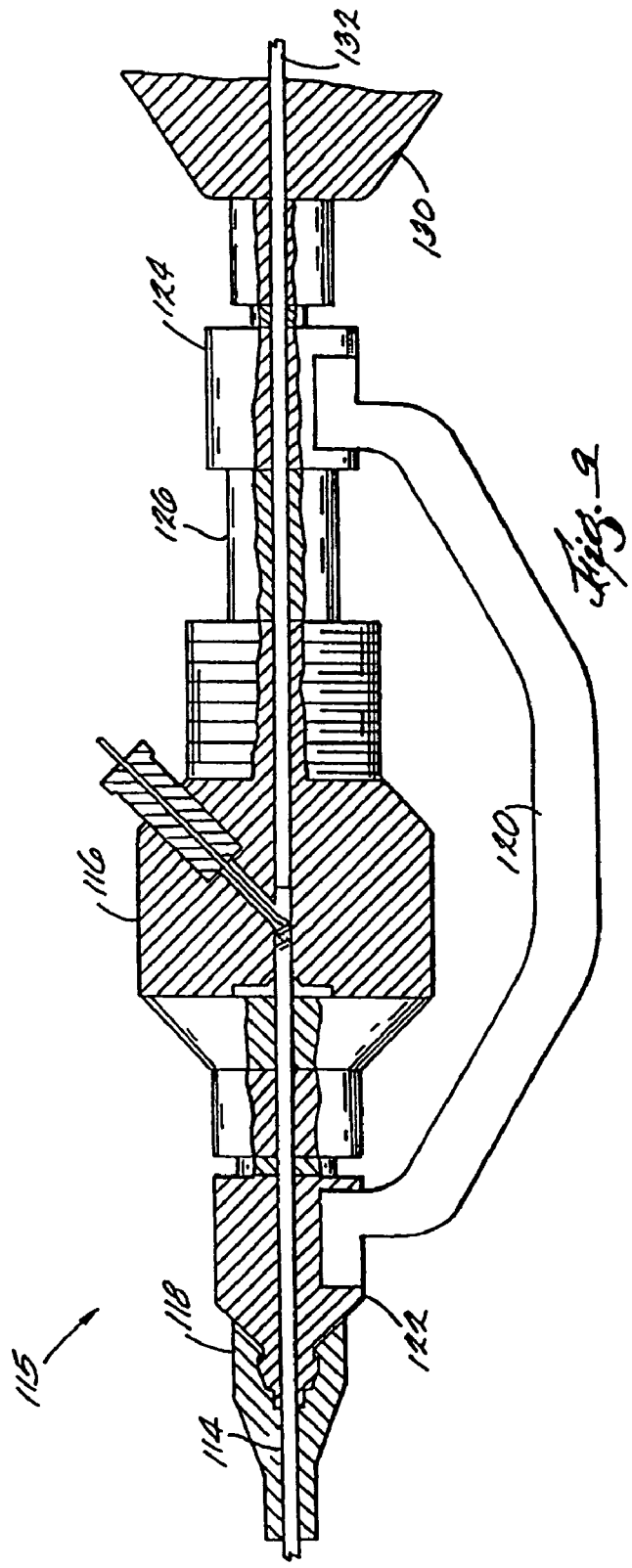

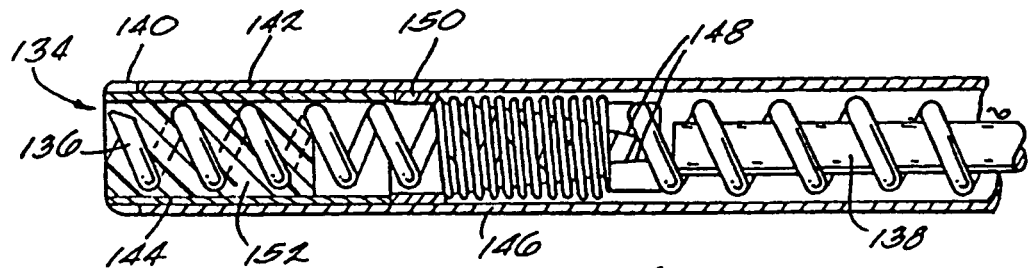
Fig. 10A
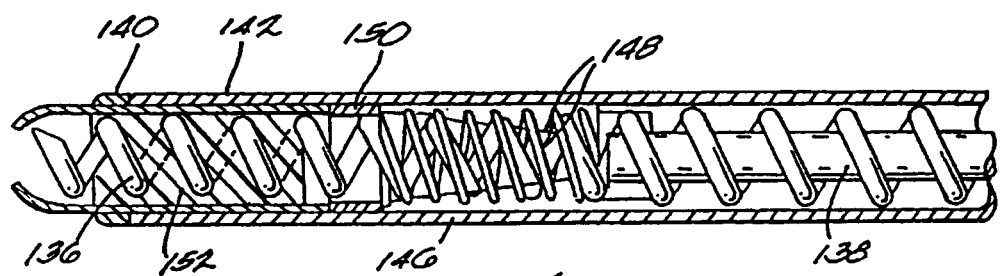
Fig. 10B
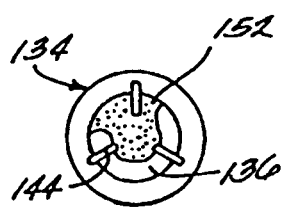
Fig. 10C
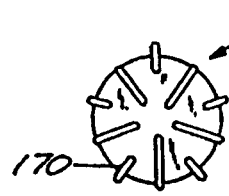
Fig. 12
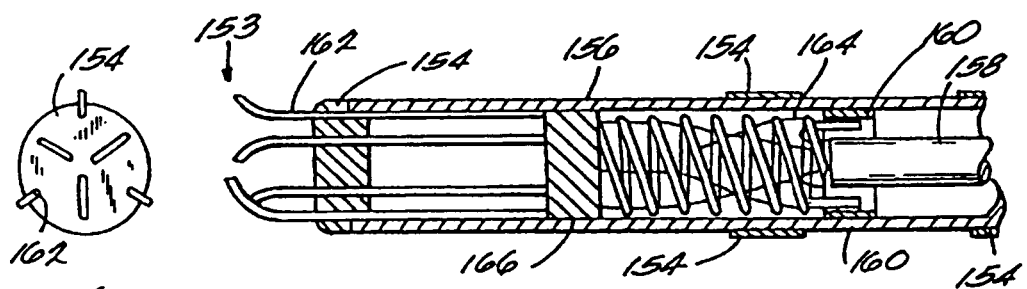
Fig. 11B
Fig. 11A

CATHETER SYSTEM AND METHODS FOR DELIVERY OF THERAPEUTIC CELLS TO CARDIAC TISSUE

CROSS-REFERENCE TO RELATED APPLICATIONS

This application is a continuation of U.S. Ser. No. 09/797,483, filed Feb. 28, 2001, which is a continuation of U.S. Ser. No. 08/403,553, filed Mar. 14, 1995, which in turn is a continuation of U.S. Ser. No. 08/100,086, filed Jul. 30, 1993, the contents of both are hereby incorporated by reference into the present disclosure.

BACKGROUND OF THE INVENTION

Abnormal heart beats or cardiac arrhythmias can cause significant morbidity and mortality. These arrhythmias arise from a variety of causes, including atherosclerotic heart disease, ischemic heart disease, metabolic or hemodynamic derangements, rheumatic heart disease, cardiac valve disease, certain pulmonary disorders and congenital etiologies. The normal heart rate is about 60 to 100 beats per minute. Arrhythmias refer to tachycardias at rates exceeding 100 beats per minute for a duration of at least 3 beats. Sometimes no treatment is required, such as in the tachycardia following a physiologic response to stress or exercise. However, in some cases, treatment is required to alleviate symptoms or to prolong the patient's life expectancy.

A variety of treatment modalities exist, including electric direct current cardioversion, pharmacologic therapy with drugs such as quinidine, digitalis, and lidocaine, treatment of an underlying disorder such as a metabolic derangement, and ablation by either percutaneous (closed chest) or surgical (open chest) procedures. Treatment by ablation involves destruction of a portion of cardiac tissue which is functioning abnormally electrically.

Normally the heart possesses an intrinsic pacemaker function in the sinoatrial (SA) node which is in the right atrium, adjacent to the entrance of the superior vena cava. The right atrium is one of four anatomic chambers of the heart. The other chambers are the right ventricle, the left atrium, and the left ventricle. The superior vena cava is a major source of venous return to the heart. The SA node is an area of specialized cardiac tissue called Purkinje cells and which usually measures roughly III centimeters by about 2 k millimeters. An electrical impulse normally exits from the SA node and travels across the atrium until it reaches the atrioventricular (AV) node. The AV node is located in the right atrium near the ventricle.

Emerging from the AV node is a specialized bundle of cardiac muscle calls which originate at the AV node in the interatrial septum. This "bundle of His" passes through the atrioventricular junction and later divides into left and right branches which supply the left and right ventricles. The left and right bundles further give rise to branches which become the so-called distal His-Purkinje system which extends throughout both ventricles.

Thus in a normal situation an impulse originates intrinsically at the SA node, transmits through the atrium and is modified by the AV node. The AV node passes the modified impulse throughout the left and right ventricles via the His-Purkinje system to result in a coordinated heartbeat at a normal rate.

Many factors affect the heart rate in addition to the intrinsic conduction system. For example, normally the heart rate will respond to physiologic parameters such as stress, exercise, oxygen tension and vagal influences. Additionally, there are multiple causes for an abnormal heartbeat such as an abnormal tachycardia. One group of such causes relates to abnormalities in the heart's conduction system. For example, ectopic or abnormally positioned nodes may take over the normal function of a node such as the SA or AV node. Additionally, one of the normal nodes may be diseased such as from ischemic heart disease, coronary artery disease or congenital reasons. Similarly, a defect can exist in an important part of the conduction system such as the bundle of His or one of the bundle branches supplying the ventricles.

Treatment of abnormal tachycardias arising from ectopic foci or so-called ectopic pacemakers can include pharmacologic therapy or ablative therapy. The ablative therapy may be accomplished by percutaneous insertion of a catheter or by an open surgical cardiac procedure.

Cardiac arrhythmias may be abolished by ablating the tissue responsible for the genesis and perpetuation of the arrhythmias. Steerable ablation catheters using radio frequency (RF) energy are known. The RF energy can be directed to the area to be ablated and causes destruction of tissue by heat. In addition, direct infusion of ethanol has been performed during open heart surgery. Ethanol has also been infused into coronary arteries to ablate a focus such as a ventricular arrhythmia focus or the AV node. Unfortunately this tends to result in a fairly large region of cardiac tissue death or myocardial infarction. With transarterial infusion there is difficulty in precisely controlling the location and extent of the ablation.

Thus, the prior art lacks catheters useful for direct endocardial infusion of sclerosing agents at the precise location of tachycardia. The present invention addresses these and other needs.

SUMMARY OF THE INVENTION

The present invention is directed to methods and devices for delivery of desired compounds (e.g., ablation liquids) to cardiac and other tissue using a novel hollow infusion needle. The needle is typically used to inject an ablation liquid endocardially to produce a more circumscribed lesion than that possible using prior art infusion techniques. The needle is designed such that it can be imbedded in and secured to the tissue to be treated.

Although ablation of cardiac tissue is a preferred use of the catheters of the invention, they can be used to inject desired compositions for a wide variety of uses. Virtually any therapeutic compound can be delivered intracardially using the catheters of the invention. For instance, the catheters can be used to deliver compositions comprising modified genes to cardiac or other tissue for use in gene therapy protocols. Methods for introducing a variety of desired polynucleotides to target cells using, for example, retroviral vectors are well known. Examples of sequences that may be introduced include antisense polynucleotides to control expression of target endogenous genes. In addition, genes encoding toxins can be targeted for delivery to cancer cells in tumors. In other embodiments, homologous targeting constructs can be used to replace an endogenous target gene. Methods and materials for preparing such constructs are known by those of skill in the art and are described in various references. See, e.g., Capecchi, Science 244:1288 (1989).

Other uses include intramyocardial delivery of isolated cells or cell substitutes. These approaches typically involve placement of the desired cells on or within matrices or membranes which prevent the host immune system from attacking the calls but allow nutrients and waste to pass to and from the calls (see, Langer et al., Science 260:920-925 (1993)). For instance, sinus node cells can be implanted in a desired location to treat disorders in impulse formation and/or transmission that lead to bradycardia.

For use in ablation of cardiac tissue, the catheters of the invention have an elongated flexible body and a tissue ablation assembly having a tissue ablation tip, at the distal end of the body. The distal end of the catheter is introduced into a cardiac chamber (or other body region) including the tissue to be ablated. The catheter may be equipped for standard arrhythmia mapping, for example multiple electrodes may be present on the outside of the catheter for recording endocardial electrograms. Alternatively, the catheter may include a visualization assembly at the distal end of the body. The visualization assembly is used to position the tip of the catheter adjacent the tissue to be ablated. Catheters comprising visualization and ablation means are described in copending application, patent application Ser. No. 08/099/995, now U.S. Pat. No. 5,385,148, which is incorporated herein by reference.

The tissue ablation assembly comprises a hollow infusion needle which can be extended or withdrawn from the distal end of the catheter. The hollow infusion needles of the invention have a securing element configured to engage tissue when the needle is at least partially inserted into the tissue to stop recoil and help prevent inadvertent removal of the needle from the tissue. The securing element can be configured into the form of corkscrew or threads surrounding a straight needle. Alternatively, the securing element can be configured as a plurality of pre-curved needles, which curve towards or away from the longitudinal axis of the catheter. The pre-curved needles can also be used to deliver ablation compounds of desired. Other structures, such as barbs, could also be used as the securing element. The hollow infusion needle is preferably a corkscrew-shaped needle, with a tight curl. The distance between turns is preferably about 0.5 mm or less. Such a needle allows the practitioner to inject through layers by slowly extending the needle, injecting, extending farther and injecting again.

When used to ablate tissue the catheter can be used with a conventional ablation compounds such as alcohol (e.g., ethanol), collagen, phenol, carbon dioxide and the like. The solution may comprise various components for other purposes as well. For instance, an echocontrast agent for echo imaging may be included. Collagen can also be bound to an iodinated molecule to make it radiodense. Alternatively, when used for gene therapy protocols, the catheters of the invention can be used to introduce desired polynucleotides to the target tissue.

When performing a percutaneous or closed chest cardiac ablation procedure using the catheters of the invention, fluoroscopy can be used to visualize the chambers of the heart. Fluoroscopy uses roentgen rays (X-rays) and includes use of a specialized screen which projects the shadows of the X-rays passing through the heart. Injectable contrast agents to enhance the fluoroscopic picture are well known in the art and are not described in detail here.

Typically, the catheter is placed in an artery or a vein of the patient depending on whether the left (ventricle and/or atrium) or right (ventricle and/or atrium) side of the heart is to be explored and portions thereof ablated. Frequently an artery or vein in the groin such as one of the femoral vessels is selected for catheterization. The catheter is passed via the blood vessel to the vena cava or aorta, also depending on whether the right or left side of the heart is to be catheterized, and from there into the appropriate atrium and/or ventricle.

The catheter is generally steerable and it is positioned against an endocardial region of interest. As mentioned above, the catheter typically includes a means for sensing the electrical impulses originating in the heart. Thus, the electrode catheter can provide a number of electrocardiogram readings from different areas of the internal aspects of the heart chambers. These various readings are correlated to provide an electrophysiologic map of the heart including notation of normal or abnormal features of the heart's conduction system. Once the electrophysiologic map is produced, an area may be selected for ablation.

Typically, before final ablation, the suspect area is temporarily suppressed or deadened with a substance such as lidocaine or iced saline solution. Subsequently the area is remapped and the heart reevaluated to determine if the temporary measure has provided some electrophysiologic improvement. If improvement has occurred, then the clinician may proceed with permanent ablation typically using ethanol.

In one aspect, the present invention provides the novel combination of tissue ablation and tissue imaging in a single catheter to permit ablation of tissue to be properly accomplished by the correct selection of the ablation site and monitoring and controlling the ablation of the tissue being destroyed. The invention is preferably used with imaging ultrasonic transceivers in an ablation catheter to provide real time assessment of lesion volume and to monitor the tissue being ablated. Alternatively, one or more A-mode ultrasonic crystals can be used. As used herein, a visualization means of the invention may be either an imaging or an A-mode ultrasonic device. One or more transponder can also be used to assist in localizing the catheter tip.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall view of a catheter made according to the invention;

FIG. 2 is an enlarged, simplified cross-sectional view of the distal end of the flexible body of FIG. 1;

FIG. 3 is an enlarged, schematic cross-sectional view of the distal end of the flexible body of FIG. 1 illustrating the general locations of the tip electrode, ultrasonic transducer, and ring electrodes;

FIG. 4 is an overall view of an alternative catheter made according to the invention;

FIG. 8 is an enlarged, simplified cross-sectional view of the tip of a catheter with a hollow needle retracted.

FIG. 9 illustrates the handle assembly of a catheter of the invention.

FIG. 10A is an enlarged, -simplified cross-sectional view of the tip of a catheter with the anchoring needles and hollow needle in the retracted position.

FIG. 10B is an enlarged, simplified cross-sectional view of the tip of a catheter with the anchoring needles and hollow needle in the extended position.

FIG. 10C is an end view of the catheter tip in FIG. 10B.

FIG. 11A is an enlarged, simplified cross-sectional view of the tip of a catheter with the anchoring/infusion needles in the extended position.

FIG. 11B is an end view of catheter tip in FIG. 11A.

FIG. 12 is an and view of a catheter tip with 10 anchoring/infusion needles.

DESCRIPTION OF THE PREFERRED EMBODIMENT

Figure 5:
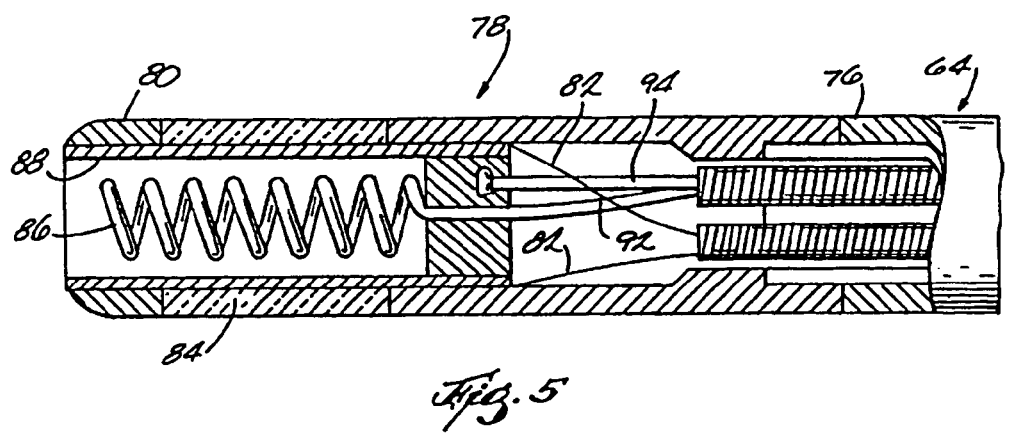
FIG. 5 is an enlarged, simplified cross-sectional view of the tip and the catheter of FIG. 4, shown with a hollow needle retracted.
Figure 6:
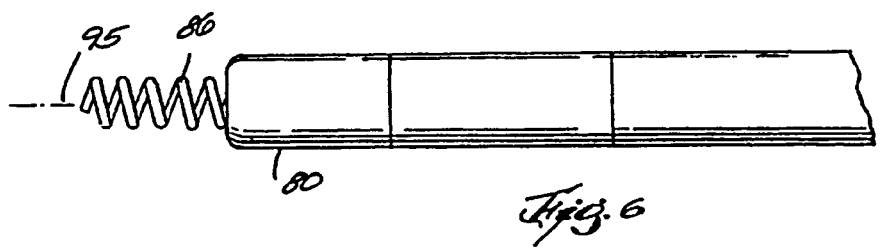
FIG. 6 is an external view of the tip of FIG. 5 with the hollow needle extended.
Figure 7:
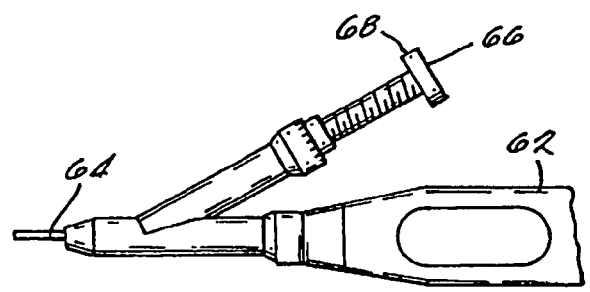
FIG. 7 is an enlarged view of the needle driver and infusion port mounted to the handle of FIG. 4.

FIG. 1 illustrates a catheter 2 having a handle 4 from which a flexible body 6 extends. Flexible body 6 extends from one end 8 of handle 4 while ultrasonic cable 10 and a combination electrode/thermistor cable 12 extend from the other end 14 of handle 4. Distal end 16 of flexible body 6 is steerable, as suggested by the dashed lines 18 in FIG. 1, in a conventional manner using a steering lever 20 mounted to handle 4. Lever 20 which controls one or more steering cables 22, see FIG. 2, as is conventional. Distal end 16 has an RF transmitting tip 24 secured thereto. Transmitting tip 24 is connected to an appropriate RF energy source, not shown, through lead 26 which extends along flexible body 6, through handle 4 and through combined cable 12.

Tip 24 has a pair of axially extending bores 28, 30 formed from its distal end 32. Bore 28 is used to house an ultrasonic transducer 34 while bore 30 is used to house a thermistor 36. Transducer 34 is surrounded by a thermal insulating sleeve 38, typically made of insulating material such as polyimide. The base 40 of transducer 34 has a lead 41 extending from transducer 34, along flexible body 6, through handle 4 and through ultrasonic cable 10. The ultrasonic transducer comprises a piezoelectric crystal capable of operating at a standard frequency, typically from about 5 to about 50 MHz. The crystal is formed from standard materials such as barium titanate, cinnabar, or zirconate-titanate. The transducer 34 generates an ultrasonic pulse in response to electrical impulses delivered through lead 41. Ultrasonic echoes are then received by the ultrasonic transducer 34 which generates electrical signals which are delivered to the receiving unit (not shown). The transducer is connected to conventional transmitting and receiving units which include the circuitry necessary for interpreting the ultrasonic information and displaying the information on a visual display. Signal processing may take advantage of change in tissue density or texture as correlated with lesion depth. The ultrasonic signal can be visualized on a two dimensional echocardiograph or using non-imaging A-mode.

Base 40 of transducer 34 is sealed with a UV potting adhesive 42, such as Tough Medical Bonder made by Loctite, to provide both thermal and electrical insulation. The catheter also comprises an ultrasonic transponder 44, shown schematically in FIG. 3, spaced about 2.5 mm from RF transmitting tip 24 at the distal end 16 of body 6. Transponder 44 is used to help in localization of the catheter tip as is known in the art and described in Langberg et al., JACC 12: 218-223 (1988). In alternate embodiments, multiple transponders can be used to help with assessing catheter tip orientation as well.

In the embodiment of FIGS. 1-3, the ablation apparatus exemplified by the use of RF transmitting tip 24. In addition to tip electrode 24, catheter 2 also includes three ring electrodes 46, 47, 48 positioned in a proximal direction, that is towards handle 4 relative to tip electrode 24 and transducer 44. Electrodes 46-48 (spaced 2.5 ma apart) are used to record electrical signals produced by the heart (electrocardiograms) for endocardial mapping using a multichannel EKG machine as is known n e art. Thermistor 36 is coupled to combination cable 12 through a lead 50 extending from thermistor 36, to flexible body 6, through handle 4 and into combination cable 12. Thermistor 36 is used to provide information about the temperature of the tissue at the distal end 32 of tip 24.

Separately, the above-discussed apparatus used to create ultrasonic visualization of the tissue to be ablated is generally conventional. An discussed above, the ultrasonic visualization means may be used for either imaging or A-mode. One such ultrasonic imaging system is sold by Cardiovascular Imaging systems of Sunnyvale, Calif. Similarly, the RF ablation system, used to ablate the tissue, is also generally conventional, such as is sold, for example, by EP Technologies of Sunnyvale, Calif. What is novel is incorporating both the imaging and ablation structure into a single catheter which permits real time visualization and accurate positioning of the RP transmitter tip 24 with the precise location to be ablated. The amount or volume of tissue ablated can thus be constantly monitored during the procedure so that neither too little nor too much tissue is ablated for maximum control and effectiveness. The use of temperature monitoring using thermistor 36 is also generally conventional as well, but not in conjunction with an ultrasonic imaging assembly. Instead of using RF energy to ablate the tissue, microwave radiation, laser energy, cryoblation or endocardial injection/infusion, for example, can be used in conjunction with ultrasonic transducer 34.

The use of catheter 2 proceeds generally as follows. Distal end 16 of body 6 is directed to the appropriate site using conventional techniques and steering lever 20. Visualization of the tissue to be ablated and localization of the tip 24 is provided by ultrasonic transducer 34, ultrasonic transponder 44, and associated leads and cables coupled to a conventional ultrasonic imagining console, not shown. When tip 24 is at the site of the tissue to be ablated, RF generator, not shown, coupled to combination cable 12, is activated to produce RF radiation at tip 24 to ablate the tissue. The ablation is monitored by ultrasonic transducer 34 as well as thermistor 36 to help ensure that the proper volume of tissue is ablated. When the proper volume of tissue is ablated, body 6 is removed from the patient. Instead of the use of catheter 2 including an RF transmitter tip 24, the catheter could use an ablation fluid infusion tip similar to that shown in FIGS. 4-7. Also, preparatory to the ablation sequence, the suspect area can be temporarily suppressed or deadened using catheter 60 using lidocaine or iced saline solution, as discussed in the Background section above.

Referring the reader now to FIGS. 4-7, a catheter 60 is shown. catheter 60 includes a handle 62 from which a flexible body 64 extends. Handle 62 includes a steering lever 65 and combination infusion port 66 and needle driver 68 at the distal end 70 of handle 62. A pair of cables 72 extend from the proximal end 74 of handle 62. The distal end 76 of flexible body 64 has a tip assembly 78 mounted thereto. Tip assembly 78 includes mapping electrodes So connected to wires 82 which extend down flexible body 64, through handle 62 and to cables 72. Mapping electrodes 80 provide the user with a nonvisual indication of where tip assembly is by monitoring the electro-activity of the heart muscle, as is conventional.

Electrodes So are electrically isolated from the remainder of tip assembly 78 by an insulating sleeve 84.

A hollow needle 86 is slidably mounted within a second insulating sleeve 88 housed within insulating sleeve 84. The needle may be formed from standard metal alloys such as titanium alloy, stainless steel, and cobalt steel. The needle 86 is a corkscrew-shaped needle used to inject ablating liquid into tissue and secure the needle to the tissue. Other designs of hollow needles, including the use of barbs on a straight or curved needle, can be used as well. While hollow needle 86 is shown sued with a generally conventional mapping electrode type of catheter, it could be used with an ultrasonic visualization assembly as shown in FIGS. 1-3, as well as other types of visualization assemblies.

A central bore 90 of hollow needle 86 is coupled to infusion port 66 by an infusion fluid tube 92 which extends along flexible body 64, through needle driver 68 and to infusion port 66. Threaded needle driver 68 is connected to a tip extension 94 so that rotating needle driver 68 causes tip extension 94 to rotate about the axis 95 of needle 86 and to move axially within flexible body 64. This causes hollow needle 86 to rotate about axis 95 and to move axially within sleeve 88 from the retracted position of FIG. 5 to the extended position of FIG. 6.

Rotating needle driver 68 also rotates hollow needle 86 so that it bores into the tissue to be ablated. When properly in position, an appropriate liquid, such as ethanol, can be infused into the tissue to be ablated through infusion port 66, infusion fluid tube 92, hollow needle 86, and into the tissue. Since the tip 100 of hollow needle 86 is buried within the tissue to be ablated, the operator is assured that the ablation liquid is delivered to the proper place while minimizing ablation of surrounding tissue.

Turning now to FIG. 8, the distal end 102 of a catheter of the present invention is shown. The hollow corkscrew infusion needle 104 is movably positioned within flexible distal tube 106. The flexible tube 106 allows movement of the distal end 102 in response to the steering mechanism 112. The steering mechanism 112 is conventional and functions as is known in the art. The distal end 102 also comprises mapping electrodes 108 which monitor electro activity of the heart muscle as described above. The mapping electrodes are connected through signal wires 111 to standard multichannel EKG machine as is known in the art.

The braided torque tube 114 is connected to the inside diameter of the infusion needle 104 and provides means for rotating the infusion needle 104 about the longitudinal axis 105 of the catheter and moving the needle 104 axially within the distal tube 106. The braided torque tube 114 consists of standard flexible tubing overlapped with a wire braid which stiffens the tube and allows torquing of the tube to rotate the needle 104.

FIG. 9 shows the handle assembly 115 of a catheter of the present invention. The braided torque tube 114 is connected to an infusion needle advance/retract knob 116 by which the user controls axial movement of the infusion needle 104. A female luer lock infusion port is positioned on the advance/retract knob 116. A standard strain relief means 118 prevents kinking of the flexible tube 119. Also provided is a handle 120 secured to the catheter through front handle support 122 and rear handle support 124. The handle assembly 115 is attached to a standard steering/mapping catheter handle 130 as is conventional and signal wires 132 are connected to the appropriate receiving units.

FIGS. 10A through 10C show the distal end 134 of a catheter comprising an infusion needle 136 connected to a braided torque tube 138 as described above. The distal tube 142 also comprises an elastomeric seal 152 made from standard materials well known to those of skill in the art. The elastomeric seal 152 provides a seal for the distal tube 142 and prevents blood from flowing into the lumen of the catheter. Typically, the infusion needle 136 is coated with a compound such as mold release, to facilitate movement of the needle through the elastomeric seal 152.

Also included in this embodiment is a set of spring loaded pre-curved anchoring needles 144 positioned near the outer edge of the distal tube 142. The anchoring needles are attached to a shuttle 150 and compression spring 146 which are triggered through pull wires 148 through a trigger device on the handle. The function of the trigger device is shown more fully in FIG. 13A, 13B and 14.

FIG. 10B shows the extended anchoring needles 144 after the triggering device has released the shuttle 150 and compression spring 146. This mechanism permits the distal end of the catheter to be attached in an almost instantaneous fashion and eliminates the effects of cardiac motion on the attachment procedure. FIG. 10C is an end view of the distal end 134 showing the position of the pre-curved anchoring needles 144 after release. In the embodiment shown here, the anchoring needles 144 are curved towards the longitudinal axis of the catheter. The anchoring needles 114, however, can be curved towards or away from the longitudinal axis.

FIGS. 11A and 11B show a further embodiment of the catheter comprising anchoring needles 162 which are used for infusion as well as anchoring. In this embodiment, the needles 162 are connected to infusion channel 160 through which the ablation liquid or other compound is delivered to the infusion needles 162. The infusion needles 162 are shown in the extended position after the shuttle 166 and compression spring 164 have moved the needles 162 axially through the distal tube 156. As with other embodiments, map electrodes 154 can be used to create an electro physiological map of the tissue. Braided tube 158 is used to anchor the compression spring 164. The infusion needles are curved outward as well as inward in this embodiment (FIG. 11B).

FIG. 12 is an end view of the distal end 168 of a catheter of the invention showing the arrangement of infusion needles 170 in which five needles project away from the longitudinal axis and five project toward the axis.

Figure 13A:
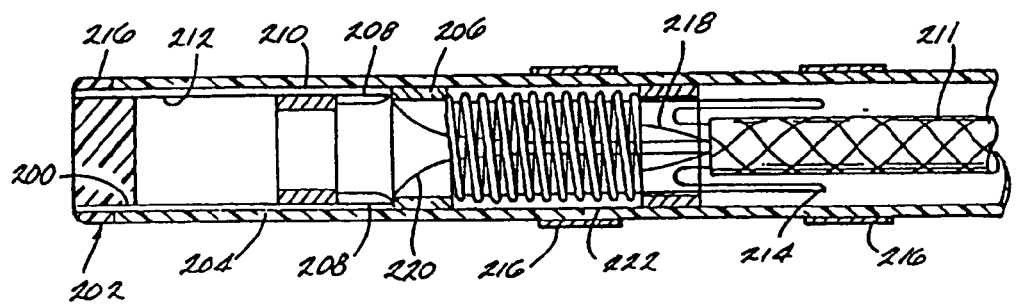
FIG. 13A is an enlarged, simplified cross-sectional view of the tip of a catheter showing the triggering mechanism with the anchoring/infusion needles in the retracted position.
Figure 13B:
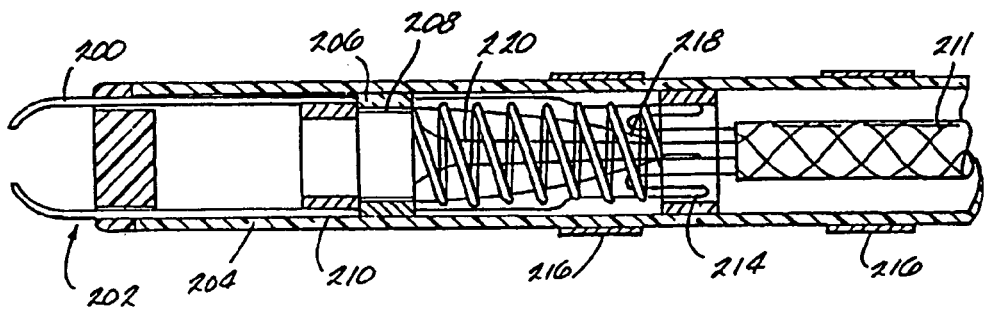
FIG. 13B is an enlarged, simplified cross-sectional view of the tip of a catheter showing the triggering mechanism with the anchoring/infusion needles in the extended position.
Figure 14:
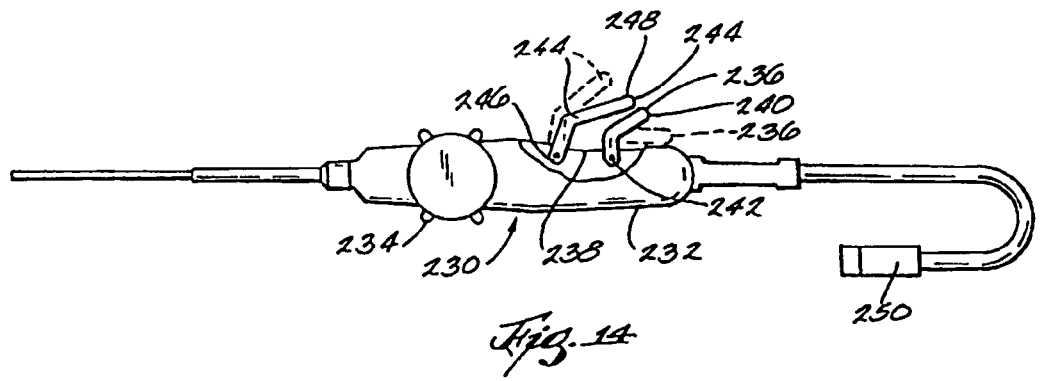
FIG. 14 illustrates the handle assembly of a catheter of the invention showing the trigger for releasing and retracting the anchoring needles.

FIGS. 13A and 13B illustrate the trigger assembly by which the pre-curved needles 200 are released from the distal end 202 of the catheters of the present invention. FIG. 13A shows the pre-curved needles 200 in the retracted position within the flexible distal tube 204. The pre-curved needles 200 are attached to the shuttle 206 which is held in place by three trigger tabs 208, two of which are illustrated in FIG. 13A. The trigger tabs 208 are permanently fixed to the front stop 210 and pre-loaded against the inner diameter 212 of the distal tube 204.

As in the other embodiments disclosed above, the pre-curved needles 200 are fluidly connected to infusion channel 214, which enters the flexible distal tube distal 204, through braided tube 211. Map electrodes 216 are used to create an electro physiological map of the heart as described.

FIG. 13B shows the pre-curved needles 200 in the extended position after the trigger tabs 208 have been pulled towards the longitude axis of the catheter by the trigger pull wires 220. Once the trigger tabs 208 have been pulled towards the longitude axis, the shuttle 206 is released and the compression spring 222 drives the shuttle 206 and needles 200 rapidly towards the distal tip of the catheter. The inertia of the catheter body prevents the tip from withdrawing and needles 200 are subsequently driven into the target tissue. FIG. 13B also shows the position of the trigger tabs 208 an the inner diameter of the shuttle 206 after the shuttle 206 has moved forward. After use the shuttle pull wires 218 are activated to pull the pre-curved needles 200 to the retracted position.

FIG. 14A shows the handle assembly 230 comprising a handle body 232 from which this position and ablation tip steering lover 234. The handle body 232 comprises a needle trigger 236 Which is shown in both the cocked and fired (dashed lines) positions. The distal end of the trigger wires 238 are attached between the distal end 240 and the pivot point 242 to insure the wires 238 are pulled when the lever is pulled. The retractor 244 is shown in the cocked and fired (dashed lines) positions, as well. The pull wires 244 are attached between the pivot point 246 and the distal end of the retractor 248 as for the trigger. The handle assembly includes a lead 250 which allows for connection to appropriate ablation compound as described above.

Modification and variation can be made to the disclosed embodiments without departing from the subject of the invention as defined in the following claims.

I claim as my invention:

1. A method for delivering therapeutic cells into cardiac tissue in a heart, said method comprising:
   advancing an elongated catheter body through a blood vessel to an endocardial delivery site in a cardiac chamber of the heart;
   advancing an end of a hollow penetrating structure from the elongated catheter body through the endocardial cardiac delivery site into the cardiac tissue; and
   delivering the therapeutic cells into the cardiac tissue through the hollow penetrating structure.

2. A method as in claim 1, wherein advancing comprises steering the catheter to engage the cardiac delivery site.

3. A method as in claim 2, wherein steering comprises pulling cables to steer a distal portion of the catheter body.

4. A method as in claim 1, further comprising securing the end of the hollow penetrating structure into the endocardium while the therapeutic compound is being delivered.

5. A method as in claim 1, wherein securing comprises penetrating an element selected from the group consisting of an element having a corkscrew-shaped distal portion, a barb, and a pre-curved needle into tissue at the cardiac delivery site.

6. A method as in claim 1, further comprising mapping the cardiac delivery site prior to delivering the therapeutic cells.

\* \* \* \* \*